US010034791B2

(12) United States Patent
DeLuke et al.

(10) Patent No.: US 10,034,791 B2
(45) Date of Patent: Jul. 31, 2018

(54) FEEDBACK SYSTEM FOR BRACE-BASED EQUIPMENT

(71) Applicant: Wellinks Inc., New Haven, CT (US)

(72) Inventors: Levi DeLuke, New Haven, CT (US); Ellen Su, San Francisco, CA (US); Sebastian Monzon, New Haven, CT (US)

(73) Assignee: Wellinks, Inc., New Haven, CT (US)

( * ) Notice: Subject to any disclaimer, the term of this patent is extended or adjusted under 35 U.S.C. 154(b) by 409 days.

(21) Appl. No.: 14/526,688

(22) Filed: Oct. 29, 2014

(65) Prior Publication Data
US 2015/0119780 A1 Apr. 30, 2015

Related U.S. Application Data

(60) Provisional application No. 61/896,993, filed on Oct. 29, 2013.

(51) Int. Cl.
*A61F 5/02* (2006.01)
*A61B 5/00* (2006.01)
*A61F 5/01* (2006.01)

(52) U.S. Cl.
CPC ............ *A61F 5/024* (2013.01); *A61B 5/0022* (2013.01); *A61B 5/4561* (2013.01);
(Continued)

(58) Field of Classification Search
CPC ...... A61F 5/00; A61F 5/01; A61F 5/02; A61F 5/022; A61F 5/024; A61F 5/026; A61F 5/028; A61B 5/4561; A61B 5/4566; A61B 5/4833; A61B 5/68; A61B 5/6801; A61B 5/6802; A61B 5/6812; A61B 5/6823
(Continued)

(56) References Cited

U.S. PATENT DOCUMENTS 5,346,461 A * 9/1994 Heinz ............... A61F 5/028
128/121.1
6,540,707 B1 4/2003 Stark et al.
(Continued)

FOREIGN PATENT DOCUMENTS

WO WO 2015066110 5/2015

OTHER PUBLICATIONS

U.S. Appl. No. 61/896,993, filed Oct. 29, 2013.
PCT International Search Report and Written Opinion, dated Jan. 28, 2015, for PCT/US2014/062774.

*Primary Examiner* — Keri J Nelson
(74) *Attorney, Agent, or Firm* — McCarter & English, LLP

(57) ABSTRACT

A system and method for measuring and/or monitoring compliance and/or quality of brace usage is provided that includes one or more straps, one or more assemblies interacting with the one or more straps, and measurement mechanism(s) associated with the strap/assembly combination to generate information related to compliance and/or quality of brace usage. The systems and methods may be retrofit to existing scoliosis braces and may be used to transmit information to remote devices and/or processors. In addition, information concerning compliance and/or quality of brace usage may be communicated to a user and/or health care provider(s), e.g., through one or more signaling elements such as aural, visual and/or haptic signaling elements associated with the at least one assembly.

15 Claims, 10 Drawing Sheets

(52) U.S. Cl.
CPC .......... *A61B 5/4566* (2013.01); *A61B 5/4833* (2013.01); *A61B 5/6804* (2013.01); *A61B 5/6812* (2013.01); *A61B 5/6823* (2013.01); *A61B 5/6831* (2013.01); *A61B 5/6843* (2013.01); *A61B 5/7435* (2013.01); *A61F 5/01* (2013.01); *A61F 5/02* (2013.01); *A61F 5/022* (2013.01); *A61B 2562/085* (2013.01); *A61F 2005/0188* (2013.01); *A61F 2220/0025* (2013.01); *A61F 2250/001* (2013.01)

(58) Field of Classification Search
USPC .......................................................... 602/19
See application file for complete search history.

(56) References Cited

U.S. PATENT DOCUMENTS

| | | | |
|---|---|---|---|
| 6,554,781 B1 | 4/2003 | Carter et al. | |
| 6,890,285 B2 | 5/2005 | Rahman et al. | |
| 6,926,667 B2 | 8/2005 | Khouri | |
| 7,128,724 B2 | 10/2006 | Marsh | |
| 7,166,063 B2 | 1/2007 | Rahman et al. | |
| 7,182,738 B2 | 2/2007 | Bonutti et al. | |
| 7,632,216 B2 | 12/2009 | Rahman et al. | |
| 8,192,383 B2 * | 6/2012 | Polliack | A61F 5/0193 128/96.1 |
| 8,512,266 B2 | 8/2013 | Lan et al. | |
| 8,821,423 B2 | 9/2014 | Conlon et al. | |
| 8,882,852 B2 * | 11/2014 | Altobelli | A61F 5/012 602/13 |
| 8,905,958 B2 | 12/2014 | Senyei et al. | |
| 2005/0043660 A1 | 2/2005 | Stark et al. | |
| 2009/0264796 A1 | 10/2009 | Pope et al. | |
| 2011/0230806 A1 | 9/2011 | Lou et al. | |
| 2011/0273286 A1 | 11/2011 | Sklar | |
| 2011/0275939 A1 | 11/2011 | Walsh et al. | |
| 2012/0184887 A1 | 7/2012 | Wynne et al. | |
| 2013/0131674 A1 | 5/2013 | Pool et al. | |
| 2015/0051530 A1 * | 2/2015 | Noda | A61B 17/085 602/41 |

* cited by examiner

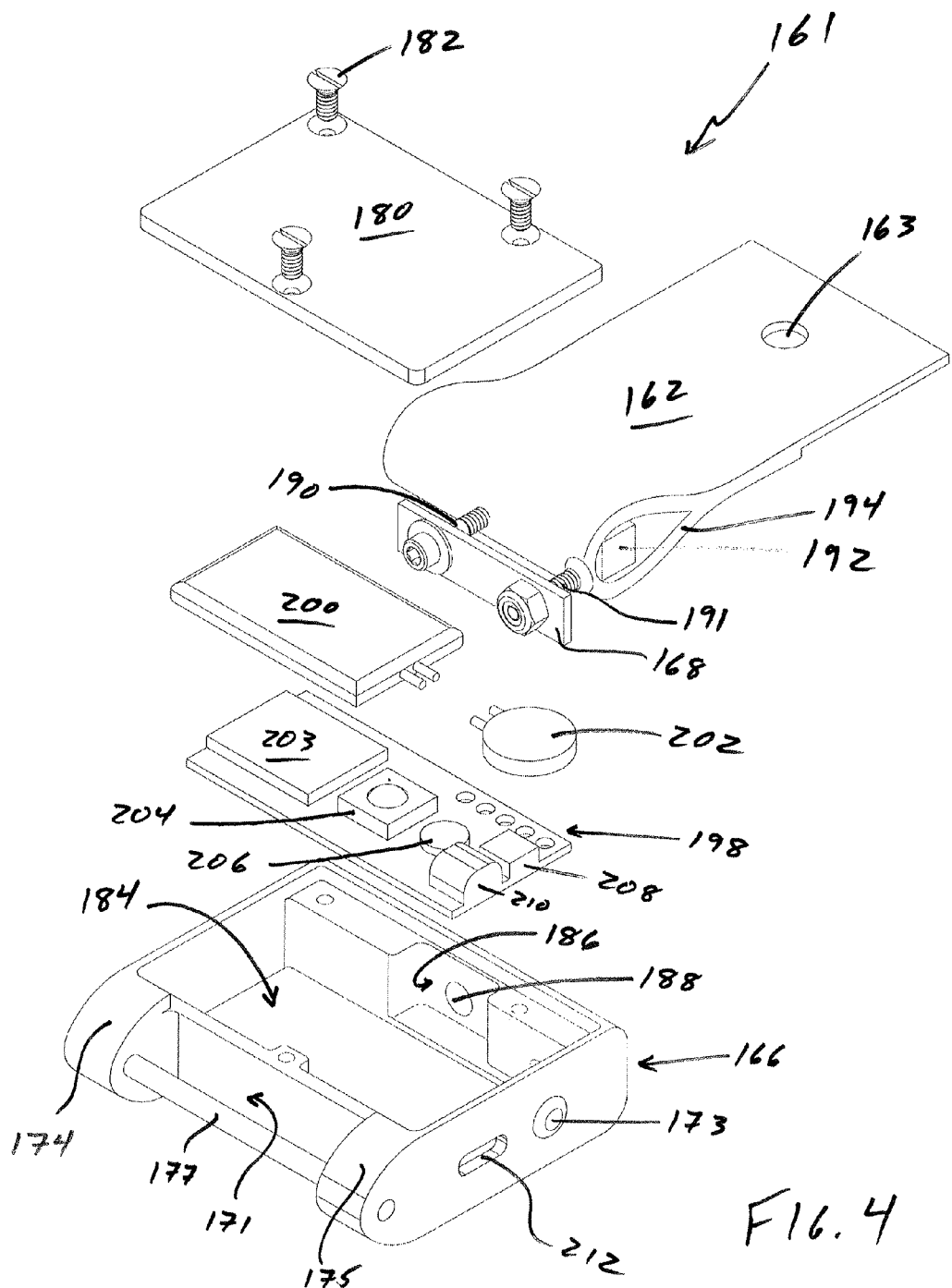

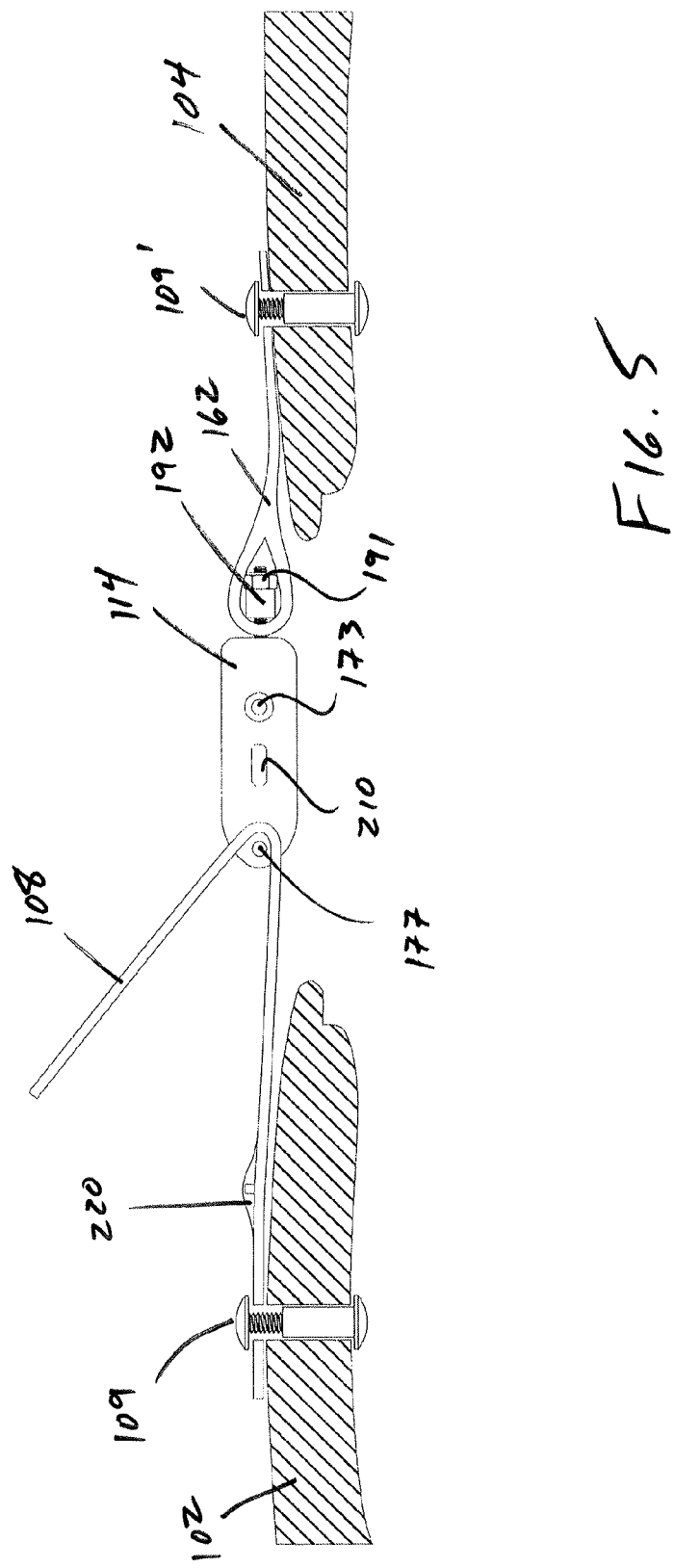

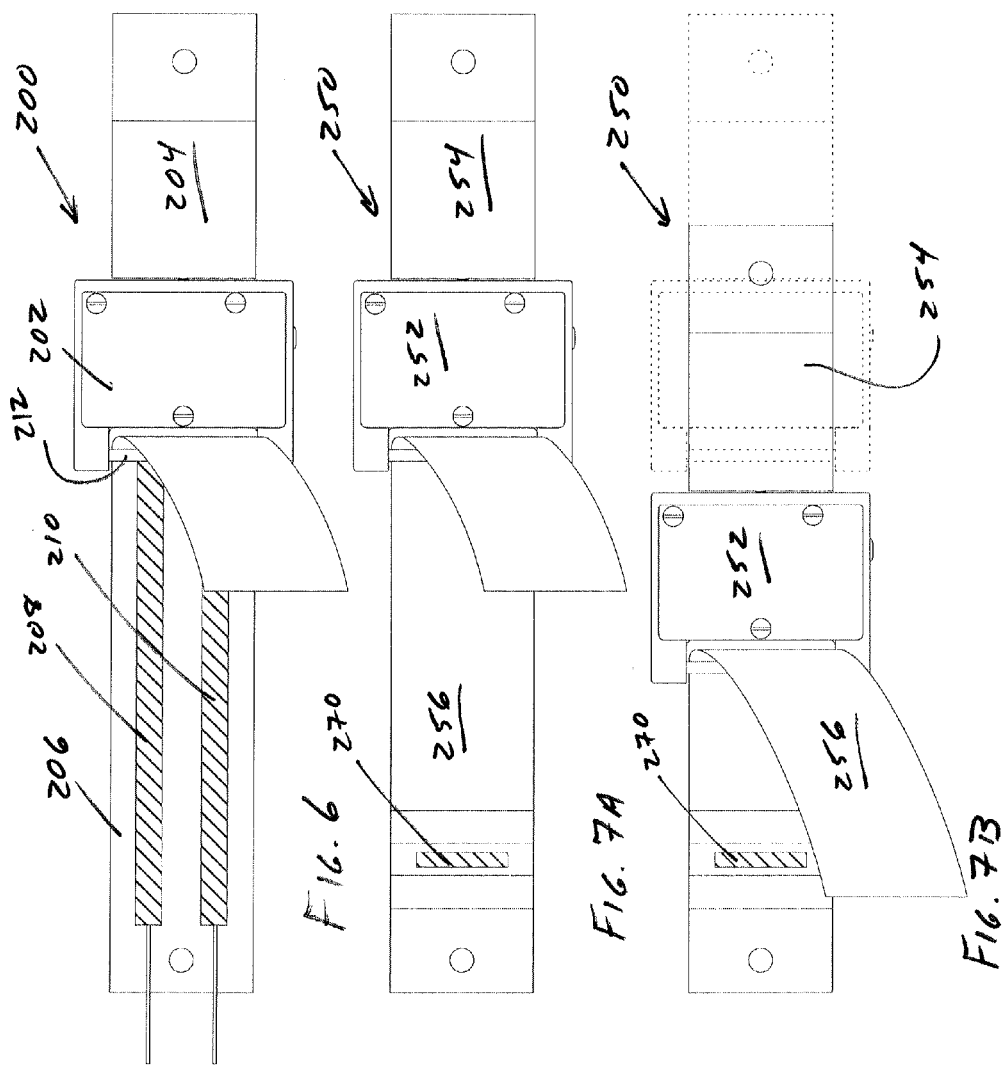

FEEDBACK SYSTEM FOR BRACE-BASED EQUIPMENT

1. CROSS-REFERENCE TO RELATED APPLICATION

The present application claims priority benefit to a provisional patent application entitled "Feedback System for Brace-Based Equipment" which was filed on Oct. 29, 2013, and assigned Ser. No. 61/896,993. The entire content of the foregoing provisional patent application is incorporated herein by reference.

BACKGROUND

2. Technical Field

The present disclosure is directed to systems and methods for monitoring and/or measuring parameters related to the use of braces in various diagnostic and/or therapeutic applications, and to communicating the monitored and/or measured parameters to data processing and/or data display units for review and/or responsive action. Exemplary implementations of the disclosed systems and methods relate to strap-based apparatus for use with scoliosis braces.

3. Background Art

The use of braces, e.g., scoliosis braces, to correct and/or limit further degradation of spinal and/or orthopedic conditions has been long-standing. Adolescent idiopathic scoliosis is a medical condition characterized by a moderate to severe curvature of the spine. Current treatment methods consist of a hard plastic brace that straightens the spine when the straps of the brace are tightened. Of note, each scoliosis brace is custom fabricated for each individual patient based on unique anatomical considerations. The information supplied to the user and/or the user's colleague(s), e.g., parent(s), is limited in terms of the use of the brace. Indeed, users and others involved in assisting users are frequently uncertain as to whether the brace is being worn properly, e.g., tightened to an appropriate degree, or for an appropriate duration.

Efforts have been made to develop compliance monitors for scoliosis braces, but those efforts have failed to yield products/systems that meet the needs of users and/or medical professionals. For example, compliance monitors that have been developed-to-date suffer from shortcomings that include (i) an inability to incorporate or integrate the compliance monitor into existing brace designs, (ii) an inability to measure both compliance and quality of brace wear, (iii) an inability to provide meaningful and/or actionable feedback to patients, colleagues of patients (e.g., parents) and/or physicians and other health care providers.

To the extent compliance monitors have been pursued, the focus-to-date has been directed to the incorporation of a temperature sensor to record how long a patient has worn the scoliosis brace. Thus, when the temperature sensor notes an elevated temperature, it is concluded that the scoliosis brace is being worn by the patient. Conversely, when an elevated temperature is absent, then it is concluded that the scoliosis brace is not being worn by the patient. As is readily apparent, the inclusion of a temperature sensor provides very limited information concerning a patient's use of a scoliosis brace. For example, no information is provided with respect to the quality of the brace's use, i.e., whether the brace is being properly worn. Moreover, the nature and quality of the information that is collected, analyzed and stored based on a temperature sensor provide little value to patients, colleagues of patients and/or physicians and other health care providers.

With reference to the patent literature, U.S. Pat. No. 6,926,667 to Khouri discloses a patient monitoring device that includes a microprocessor controller having a clock circuit and memory coupled to one or more sensors physically carried by a medical appliance, vacuum domes for enclosing the breasts of a female patient. According to the Khouri '667 patent, a pressure sensor may be provided in conjunction with one of the vacuum domes to confirm appropriate levels of negative pressure. A temperature sensor may be provided to confirm that a patient is wearing/using the medical device. A third sensor may be provided to confirm the information received from the first or second sensor. The sensors provide an electrical signal that may be timed to confirm a patient's compliance with a recommended protocol. By combining and correlating the sensor data with the clock or timer provided as part of the controller, a time chart of data may be created indicating when and for how long the patient actually wears the device.

U.S. Patent Publication No. 2009/0281469 to Conlon et al. discloses a compliance strapping that includes a predetermined adjustability, tamper deterring and indicating strapping, that is adapted, in use, to form an encircling loop. The compliance strapping is passed around an object and, for further security, the strap can be threaded through lining material or through a wearable article or medical device. The free end of the elongate member is passed through the loop, which may be a D-loop sewn into the strapping, thus forming an encircling loop of strapping. The second end is brought around to close proximity with a region of the strapping which has been passed through the loop. The tamper indicating means, known as a self-locking rivet, is fastened to this region of the strapping. Thus, the encircling loop cannot be broken because the region of the strapping with the self-locking rivet fastened thereto cannot pass back through the D-loop.

U.S. Pat. No. 6,540,707 to Stark et al. discloses an exercise orthosis that includes a frame, a fluid bladder held by the frame, a pressure sensor attached to the fluid bladder and a microprocessor for receiving pressure measurements from the pressure sensor. The microprocessor monitors variations in pressure and determines differences between the measured pressures and predetermined target values. The frame can be designed to support a hinge joint or at least one vertebra. The Stark '707 patent further discloses a corrective back orthosis that includes a frame, force applicators connected to the frame to apply force to the patient's spine, a sensor that measures forces associated with the force applicators, and a control unit that monitors forces measured by the sensor. The corrective back orthosis can include fluid bladders as force applicators and the control unit can include a microprocessor.

U.S. Pat. Nos. 6,890,285, 7,166,063 and 7,632,216 to Rahman et al. disclose brace compliance monitors. The Rahman patents generally disclose a brace compliance monitor that includes a compliance sensor, a signal processor, and a display. Compliance data from the Rahman systems is displayed on the display to provide the patient or subject with immediate compliance information on whether they have been wearing the brace for the specified period and in the specified manner. The brace compliance monitor may also include a secondary sensor, such as a tilt sensor, a pressure sensor, a force sensor, an acceleration sensor, or a velocity sensor. The secondary sensors may provide additional compliance data to the patient and health care provider.

Despite efforts to date, a need remains for systems and methods that effectively monitor and/or measure parameters related to the use of braces in various diagnostic and/or therapeutic applications. In addition, a need remains for systems and methods that effectively communicate monitored and/or measured parameters that are collected from brace-related applications to data processing and/or data display units to facilitate review and/or responsive action. More specifically, a need remains for systems and methods that can effectively determine whether a brace, e.g., a scoliosis brace, is being properly used, both as to tightness and duration of use, and communicate this information so as to permit responsive action, whether in real-time or at a point in the future. These and other needs are satisfied by the systems and methods disclosed herein.

SUMMARY

As noted above, the present disclosure is directed to systems and methods for monitoring and/or measuring parameters related to the use of braces in various diagnostic and/or therapeutic applications, and to communicating the monitored and/or measured parameters to data processing and/or data display units for review and/or responsive action. In exemplary embodiments, a strap-based feedback device is provided for use with a scoliosis brace. The feedback device includes sensing and/or feedback mechanisms integrated into or otherwise associated with one or more straps. The sensing and/or feedback mechanisms associated with the disclosed feedback device collect advantageous information as to the quality and/or compliance of brace utilization by a prescribed user. The noted information may be leveraged in various ways according to the present disclosure, e.g., providing real-time feedback to the prescribed user and his/her colleague(s) (e.g., parent(s)) and providing clinical feedback to the prescribing physician or health care provider, e.g., providing real-time or cumulatively collected information concerning brace usage and related anatomical parameters.

In exemplary implementations, the disclosed feedback device includes force and/or positioning sensing functionality associated with strap(s) that are adapted to releasably fix a brace in place. Thus, for example, a scoliosis brace may include one or more (e.g., three) straps for use in releasably fixing the brace relative to a prescribed user's spine. At least one of the straps is provided with a force sensor and/or a position sensor that is adapted to monitor and/or measure force or position, respectively. The sensor(s) are advantageously integrated with the strap(s), although it is further contemplated that the sensor(s) may be detachably secured with respect to the strap(s), e.g., using a conventional attachment mechanism such as a snap, Velcro™ or the like.

The feedback device also advantageously includes one or more communication functionalities that facilitate communication of the sensed parameters, e.g., force and/or position parameters. Exemplary communication functionalities include visual, haptic (vibratory) and/or auditory signals or cues. The foregoing signals/cues may be delivered in situ, i.e., directly from the feedback device that is integrated in or associated with the strap(s), or from a remote device, e.g., a smart/cellular phone, pager, personal digital assistant, tablet or the like. Thus, in exemplary embodiments of the present disclosure, the feedback device includes a communication capability, e.g., a short-range wireless communication transmitter that is Bluetooth compliant, that is adapted to transmit sensed parameters to a remote device, e.g., a smart/cellular phone, computer or other electronic device, for processing and/or storage.

The disclosed system and method may advantageously include and/or interact with data processing and/or analytical functionalities. Thus, the force and/or position parameters that are sensed by the disclosed feedback device may be transmitted to a remote device (either directly or by way of an associated network) that is programmed to store, process and/or analyze the sensed data. Various analytical tools may be supported by and/or incorporated in the disclosed systems and methods, e.g., analytics related to anatomical developments of the user, analytics related to usage frequency/duration, analytics related to force delivery, analytics related to brace suitability in view of user growth/development, and the like. The analytical results may be accessed by the prescribed user, by colleague(s) of the user (e.g., parents), and/or by the physician or health care provider(s). Historical information may be generated that may prove useful in longer-term treatment of the user and/or in developing a better clinical understanding of various treatment modalities.

The disclosed systems and methods may be developed and delivered in conjunction with newly manufactured braces. In addition, the present disclosure contemplates retro-fitted applications of the disclosed feedback device, e.g., through integration and/or association with existing straps or replacement straps for use with existing braces. Thus, the present disclosure provides an efficient and cost-effective design that facilitates immediate and widespread adoption and use of the disclosed systems and methods, including adoption and/or integration at various stages of the existing supply chain for braces, e.g., scoliosis braces.

Additional features, functions and benefits associated with the systems and methods will become apparent from the detailed description which follows, particularly when read in conjunction with the appended figures.

BRIEF DESCRIPTION OF FIGURES

To assist those of skill in the art in practicing the systems and methods disclosed herein, reference is made to the accompanying figures, wherein:

FIG. 4 is an exploded view of an exemplary strap and sensing assembly according to the present disclosure;

FIG. 5 is a side view, partially in cross-section, of an exemplary strap and sensing assembly mounted with respect to a brace according to the present disclosure;

FIG. 6 is a schematic view of an exemplary strap and sensing system according to the present disclosure;

FIG. 7A is a schematic view of an alternative exemplary strap and sensing system in an initial position according to the present disclosure;

FIG. 7B is a schematic view of the exemplary strap and sensing system of FIG. 7A in a second position;

DESCRIPTION OF EXEMPLARY EMBODIMENT(S)

Figure 1:
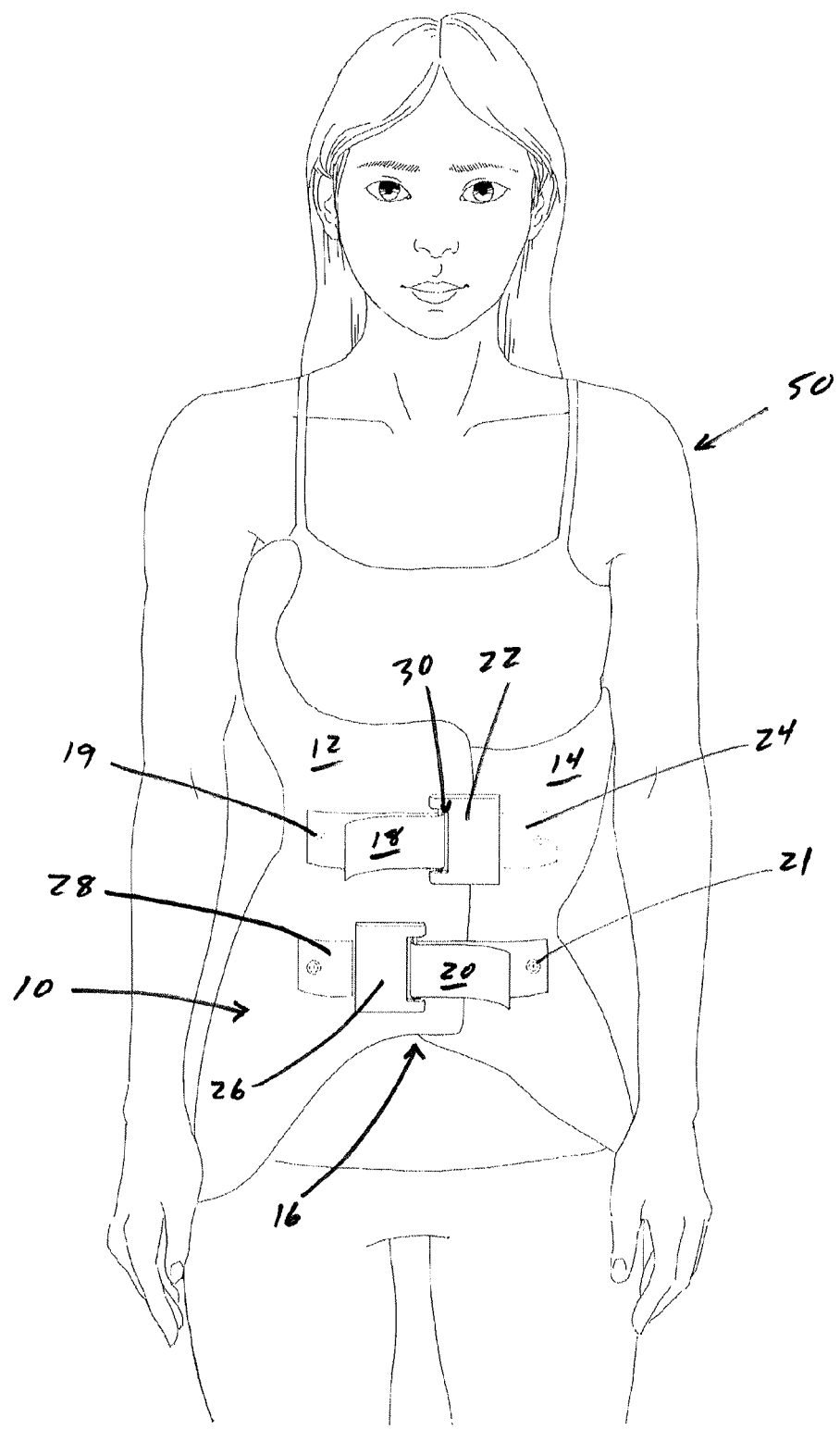
FIG. 1 is a schematic view of a multi-strap scoliosis brace system with the straps associated with the front face of the brace positioned on a user according to the present disclosure.

According to the present disclosure, systems and methods are provided for monitoring and/or measuring parameters associated with the use of braces, e.g., scoliosis braces. In exemplary implementations, the disclosed systems and methods are adapted to communicate the monitored and/or measured parameters, e.g., through visual, haptic (vibratory) and/or auditory signals or cues. Moreover, the monitored and/or measured parameters may be transmitted to a remote device that is programmed to store, process and/or analyze the data. Various analytical tools may be supported by and/or incorporated in the disclosed systems and methods, e.g., analytics related to anatomical developments of the user, analytics related to usage frequency/duration, analytics related to force delivery, analytics related to brace suitability in view of user growth/development, and the like. The analytical results may be accessed by the prescribed user, by colleague(s) of the user (e.g., parents), and/or by the physician or health care provider(s).

The compliance of brace wear is typically used in the medical literature and in practice by physicians and other health care providers to describe the amount of time a patient wears a brace as compared to the amount of time the doctor prescribes the brace to be worn. For example, if a doctor prescribes that a brace be worn twenty three (23) hours per day, but the patient only wears the brace for twelve (12) hours per day, the patient would be deemed to be fifty two percent (52%) compliant with respect to brace wear.

The quality of brace wear is distinct from compliance, and for purposes of this disclosure, is a measure of how well the brace is being worn. Quality of brace wear is distinguishable from compliance of brace wear because the brace may not be tightened completely when the patient is wearing it. In such circumstance, the patient may be deemed "compliant" because the brace is being worn, but the "quality" of brace wear is less than desirable.

The present disclosure advantageously provides systems and methods that allow the capture of metrics that may be used to evaluate both compliance and quality of brace wear. In particular, the quality of brace wear may be determined by strap tension and/or strap position, as described herein. Of note, the strap position is currently used by doctors to give patients a guide to where to tighten the brace to each day. Since the ability to reach that position can change over time (e.g., due to weight gain, eating, etc.), a better measure of quality may be achieved according to the present disclosure based on the tension of the strap, or some combination of both tension or position. The disclosed systems/methods are advantageously able to detect both the compliance and quality of brace wear, and adapt the metrics over time as determined by the physician.

Indeed, methods for measuring compliance and quality of brace wear may vary and/or evolve according to the present disclosure. Moreover, an algorithm developed to measure compliance/quality may be static or varied from time-to-time. For example, it may be desirable for an algorithm that is intended to measure compliance/quality to utilize different parameters and/or different target performance levels from time-to-time, e.g., based on the length of time that a brace user has been engaged in brace use.

Of note, the present disclosure provides systems and methods that enable measurement and communication of compliance and quality of brace wear, as well as updates, refinements and/or variations in prescriptive parameters and/or targets for brace use, e.g., based on determinations by health care professional(s) in view of reported measurements. Thus, the disclosed systems and methods permit health care professionals to update brace-based "prescriptions" at any time and from remote locations. For example, a health care professional is able to receive and evaluate compliance and quality of brace use in his/her office, and then to refine the brace-based prescription so as to enhance and/or optimize brace usage based on his/her professional judgment. Moreover, the disclosed systems and methods support and enable algorithmic-based updates, refinements and/or variations in parameters and/or targets for brace use, e.g., based on comparisons of brace-based performance parameters and target performance levels which algorithmically translate to updated, refined and/or varied brace-based usage parameters. The disclosed feedback systems and methods are generally brace specific, i.e., communications associated with updated, refined and/or varied usage parameters are specific to an individual use case, and are generally communicated by conventional communication protocols, e.g., Bluetooth communications or the like.

With initial reference to FIG. 1, a front portion of an exemplary scoliosis brace 10 shown secured to the torso of a user 50. Scoliosis brace 10 includes first and second portions 12, 14 that overlap in an interface region 16. Of note, although the exemplary embodiment of FIG. 1 depicts an overlap of first and second portions 10, 12, alternative scoliosis brace implementations may instead define a "gap" between first and second portions 12, 14. Thus, the overlap region 16 may take the form of a "gap" between cooperative portions of the disclosed scoliosis brace, and references to "overlap regions" and "gaps" should be understood to embrace the relative positioning of the first and second portions, whether such relative positioning defines spacing, overlap or even side-by-side juxtaposition.

A plurality of straps are mounted with respect to scoliosis brace 10 to facilitate securement thereof with respect to the user's torso. In particular, exemplary scoliosis brace 10 includes first strap 18 and second strap 20. As will be readily apparent to persons skilled in the art, the present disclosure is not limited to brace implementations that include two straps or to brace implementations wherein the straps are located on the front face of the brace. Rather, the present disclosure may be implemented with greater numbers of straps without departing from the spirit or scope of the present disclosure, or to rear and/or side positioning of straps. Positioning of the straps on the front face of the scoliosis brace may be preferable in specific usage environments, e.g., for night-time use.

With further reference to FIG. 1, each of the straps is fixedly mounted with respect to either the first portion 12 or the second portion 14 of scoliosis brace 10. More particularly, first strap 18 is fixedly mounted with respect to first portion 12 by attachment mechanism 19 and second strap 20 is fixedly mounted with respect to second portion 14 by attachment mechanism 21. In the disclosed embodiment, first strap 18 releasably cooperates with sensing assembly 22 that is mounted with respect to second portion 14 of brace 10 by mounting strap 24. Sensing assembly 22 provides advantageous monitoring and feedback functionality according to the present disclosure, as described in greater detail below. Similarly, second strap 20 releasably cooperates with sensing assembly 26 that is mounted with respect to first portion 12 of brace 10 by mounting strap 28. Sensing assembly 26 also provides advantageous monitoring and feedback functionality according to the present disclosure, as described in greater detail below. Each of the mounting straps 24, 28 is fixed with respect to either first portion 12 or second portion 14 of scoliosis brace 10, e.g., by way of a rivet, Chicago binding post or the like. The mounting of straps relative to scoliosis braces generally allows angular adjustment of strap orientation relative to the brace, thereby permitting effective alignment of the cooperative components of the present disclosure.

In the exemplary embodiment of FIG. 1, first strap 18 is mounted with respect to the first portion 12, whereas second strap 20 is mounted with respect to the second portion 14. The opposed fixation arrangement of the straps relative to the scoliosis brace 10 may improve the stability and/or ease with which the scoliosis brace may be brought into a desired orientation by the user. However, the present disclosure is not limited to the "opposed fixation" arrangement depicted in FIG. 1, and brace-based systems may be implemented according to the present disclosure wherein the straps are mounted with respect to the same portion of the brace without departing from the spirit or scope hereof.

Sensing assembly 22 includes a mounting passage 30 that accommodates passage of first strap 18 in a "looping" fashion relative to sensing assembly 22, thereby allowing the user 50 to pull on the free end of strap 18 to cinch second portion 14 relative to first portion 12, thereby increasing the overlap of first portion 12 relative to second portion 14. In implementations wherein a gap is defined between the first and second portions of the scoliosis brace, the cinching operation will serve to reduce the gap and/or bring the two portions into a juxtaposed or overlapping orientation. Once cinched to a desired degree, first strap 18 is generally adapted to be detachably fixed in the desired position, e.g., by way of cooperative Velcro™ interaction in the overlapping region of strap 18. Alternative fixation mechanisms may be employed to secure strap 18 in its cinched orientation, as will be readily apparent to persons skilled in the art. Similar looping, cinching and fixation mechanisms are generally provided with respect to second strap 20, thereby permitting the user to bring the first portion 12 and the second portion 14 of scoliosis brace 10 into a desired approximation.

In conventional scoliosis brace systems, the desired cinched relationship between the first portion 12 and the second portion 14 of scoliosis brace 10 is inexactly established. For example, a physician or other health care provider may apply a mark, e.g., a line, on some aspect of the scoliosis system to designate the desired spatial relationship of the first and second portions 12, 14, when in use. The user 50 then strives to bring the scoliosis system into alignment with the designated marking, subject to visibility limitations, parallax issues and difficulties in applying the requisite force to achieve the desired brace orientation. Moreover, conventional scoliosis systems provide no ability to monitor the brace orientation over a period of use and/or identify changes to applicable parameters, e.g., the user's anatomy, that may impact on the accuracy of the initial "marking" provided by the physician or other health care provider. The disclosed systems and methods overcome the noted limitations and shortcomings of existing scoliosis brace systems.

Figure 2:
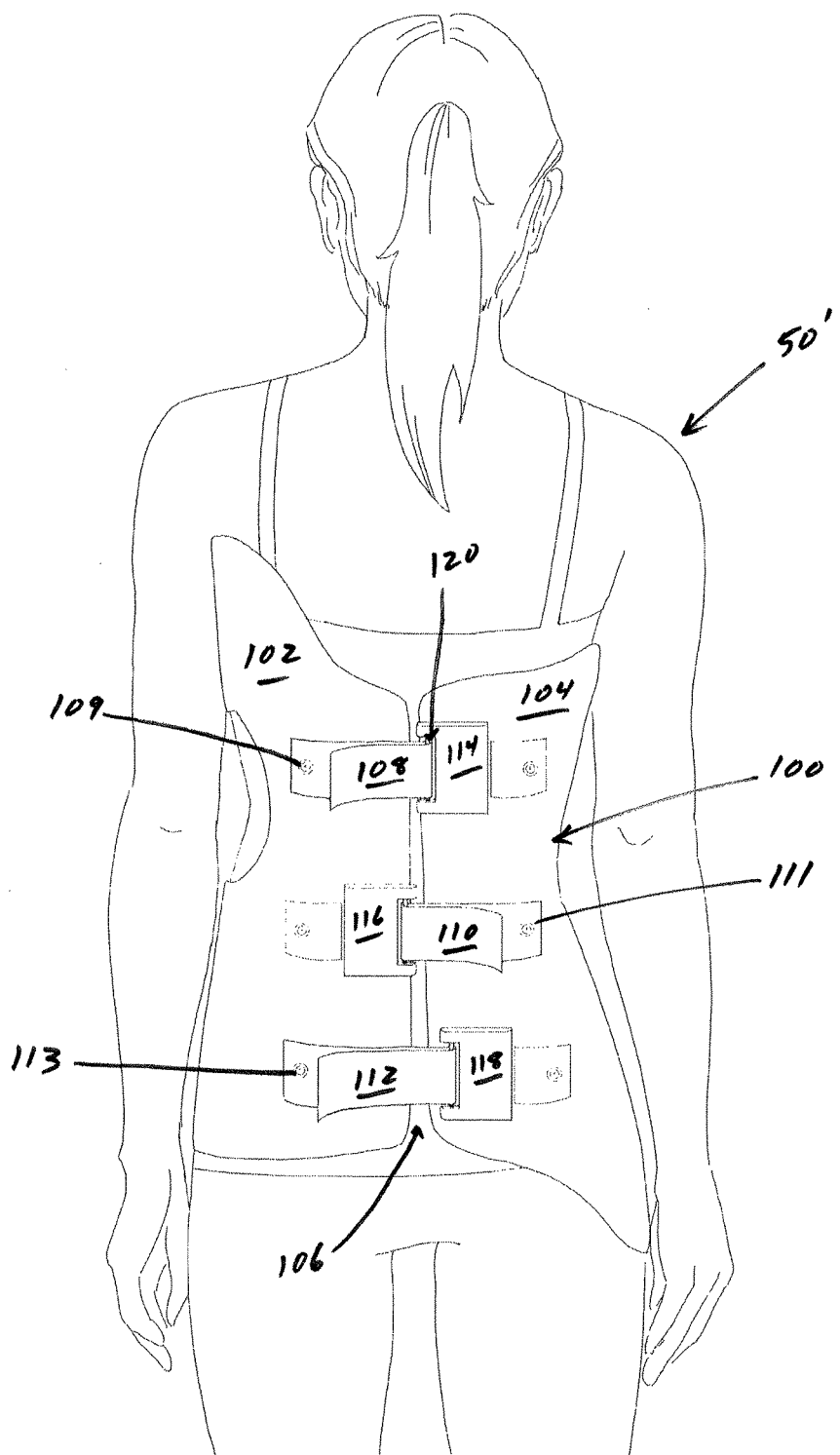
FIG. 2 is a schematic view of an alternative multi-strap scoliosis brace system with the straps associated with the rear face of the brace positioned on a user according to the present disclosure.

With reference to FIG. 2, a rear portion of an alternative scoliosis brace 100 is shown secured to the torso of a user 50'. As compared to FIG. 1, scoliosis brace 100 is cinched at the rear of user 50', as compared to brace 10 which was adapted to be cinched in the abdominal region of user 50. Rear cinching braces are generally utilized for all-day wear, i.e., rear cinching braces are frequently prescribed for up to twenty three (23) hours of usage per day). Scoliosis brace 100 includes first and second portions 102, 104 that define a gap 106 therebetween. Of note, the "gap" defined by first and second portions 102, 104 may be a spacing therebetween (as schematically depicted in FIG. 2) or an overlap of first and second portions 102, 104. Thus, as noted above, the term "gap" as used herein should be understood to embrace the relative positioning of the first and second portions, whether such relative positioning defines spacing, overlap or even side-by-side juxtaposition.

A plurality of straps are mounted with respect to scoliosis brace 100 to facilitate securement thereof with respect to the user's torso. In particular, exemplary scoliosis brace 100 includes first strap 108, second strap 110 and third strap 112. As will be readily apparent to persons skilled in the art, the present disclosure is not limited to brace implementations that include three straps. Rather, the present disclosure may be implemented with fewer or greater numbers of straps without departing from the spirit or scope of the present disclosure.

With further reference to FIG. 2, each of the straps is fixedly mounted with respect to either the first portion 102 or the second portion 104 of scoliosis brace 100. More particularly, first strap 108 is fixedly mounted with respect to first portion 102 by attachment element 109 and third strap 112 is fixedly mounted with respect to first portion 102 by attachment element 113. In the disclosed embodiment, second strap 110 is fixedly mounted with respect to second portion 104 by attachment element 111. Attachment elements 109, 111, 113 generally take the form of a rivet or like structure, thereby permitting rotational freedom so as to facilitate strap alignment in use.

Sensing assemblies 114, 116 and 118 are provided with respect to first, second and third straps 108, 110 and 112, respectively. Each of the sensing assemblies is mounted with respect to either first portion 102 or second portion 104 of scoliosis brace 100, e.g., by way of a mounting strap that is secured relative to the brace by a rivet or the like. In the exemplary embodiment of FIG. 2, two straps are fixed with respect to the first portion 102, whereas the intermediate strap is fixed with respect to the second portion 104. The alternating fixation arrangement of scoliosis brace 100 may improve the stability and/or ease with which the scoliosis brace may be brought into a desired orientation by the user, although the present disclosure is not limited by or to the disclosed alternating fixation arrangement.

Sensing assembly 114 includes a mounting passage 120 that accommodates passage of first strap 108 in a "looping" fashion, thereby allowing the user 50' to pull on the free end of strap 108 to cinch second portion 104 relative to first portion 102, thereby reducing the width of gap 106. Once cinched to a desired degree, strap 108 is generally adapted to be detachably fixed in the desired position, e.g., by way of cooperative Velcro™ interaction in the overlapping region of strap 108. Alternative fixation mechanisms may be employed to secure strap 108 in its cinched orientation, as will be readily apparent to persons skilled in the art. Similar looping, cinching and fixation mechanisms are generally provided with respect to second strap 110 and third strap 112, thereby permitting the user to bring the first portion 102 and the second portion 104 of scoliosis brace into a desired approximation.

Figure 3A:
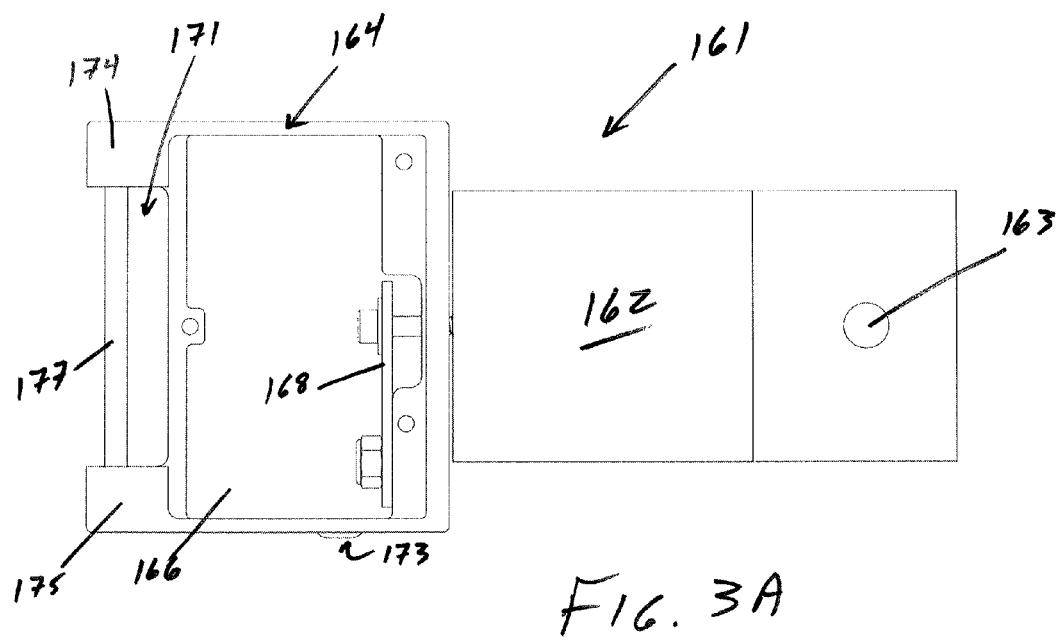
FIG. 3A is a top view of an exemplary strap and sensing assembly (with cover plate removed for viewing purposes) that facilitates monitoring and feedback relative to scoliosis brace usage according to the present disclosure.
Figure 3B:
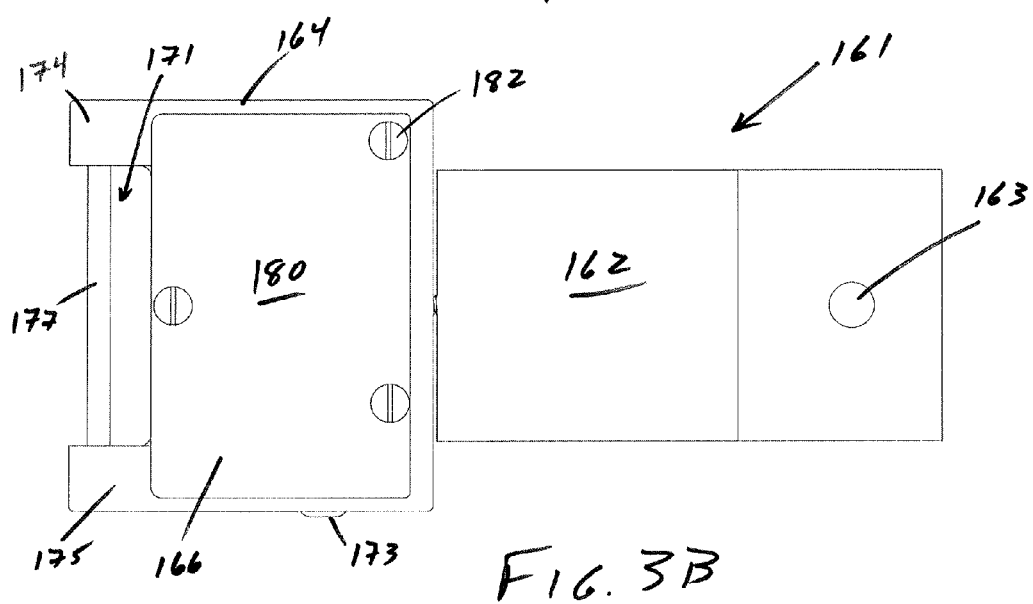
FIG. 3B is a top view of the exemplary strap and sensing assembly of FIG. 3A with a cover plate positioned thereon.

Turning to FIGS. 3A and 3B, top views of an exemplary strap and sensing assembly 161 according to the present disclosure are provided. In FIG. 3A, the top face of sensing unit 164 has been removed to facilitate viewing of internal components. Moreover, the circuit board generally associated with sensing unit 164 has also been omitted for viewing ease. The exploded view of FIG. 4 provides a detailed depiction of internal components of exemplary sensing units according to the present disclosure. Strap and sensing assembly 161 includes a strap 162 that includes an aperture 163 for use in securing the strap 162 relative to a scoliosis brace, and a sensing unit 164 that is movably mounted relative to strap 162. As noted above, strap 162 may be secured relative to a brace using various mounting systems, e.g., a rivet or the like. In terms of brace-based mounting of strap 162, it is noted that alternative mounting techniques may eliminate the need for aperture 163, as will be readily apparent to persons skilled in the art.

Sensing unit 164 generally includes a housing 166 and a gauge mechanism positioned within the housing 166 that is adapted to measure the force applied to assembly 161. In exemplary embodiments of the present disclosure, the gauge mechanism takes the form of a strain gauge 168 that is positioned within housing 166 and that is cooperatively mounted with respect to strap 162 so as to measure forces experienced thereby. A switch or button 173 typically extends through or is otherwise associated with housing 166 of sensing unit 164 to facilitate powering up or powering down of sensing unit 164. Switch or button 173 interacts with electronics within housing 166, as described herein.

Housing 166 generally defines a slot or passage 171 is configured and dimensioned to receive a strap for use with scoliosis braces. Passage 171 may be defined relative to housing 166 by extension arms 174, 175 and a rod or pin 177 that extends therebetween. Rod/pin 177 generally defines a circular or elliptical cross-section so as to facilitate interaction with a strap that passes through passage 171. Alternative structural arrangements may be employed to define a slot or passage relative to housing 166, as will be readily apparent to persons skilled in the art.

With reference to FIG. 3B, a cover face 180 is mounted with respect to housing 166 to encase the internal components thereof. Cover face 180 may be mounted to housing 166 by conventional means, e.g., screws 182. Although the housing/cover face assembly 166/180 is depicted in a substantially rectangular geometry, the present disclosure is not limited by or to the disclosed geometry.

Turning to FIG. 4, an exploded view of strap and sensing assembly 161 is provided. As shown therein, strap and sensing assembly 161 includes housing 166 that defines a cavity 184 for receipt of operative components of the disclosed sensing system. As previously noted, housing 166 defines a slot or passage 171 that is configured and dimensioned to receive a strap for use with scoliosis braces. In the exemplary implementation of assembly 161, passage 171 is defined by extension arms 174, 175 that are formed by the side walls of housing 166 and a rod or pin 177 that extends therebetween. Rod/pin 177 generally defines a circular or elliptical cross-section so as to facilitate interaction with a strap that passes through passage 171. The size and geometry of passage 171 is selected so as to permit ease of passage of a strap associated with the disclosed system. Alternative structural arrangements may be employed to define a slot or passage relative to housing 166, as will be readily apparent to persons skilled in the art.

With further reference to FIG. 4, housing 166 generally defines a recessed region 186 for receipt and support of strain gauge 168. Recessed region 186 includes a central aperture 188 for passage of strain gauge extension arm 190. Extension arm/screw 190 is mounted with respect to strap 162 so as to sense forces experienced by the strap and sensing unit 161. A second mounting arm/screw 191 is fixedly mounted with respect to strap 162 so as to fix housing 166 relative to strap 162. A mounting block 192 may be associated with a looped portion 194 of strap 162 to facilitate mounting of housing 166 relative to strap 162. Strain gauge 168 is of conventional design, as will be apparent to persons skilled in the art.

A circuit board 198 is generally positioned in cavity 184 of housing 166. Circuit board 198 is generally powered by a battery 200 which is also positioned within cavity 184 and which is in electrical communication with circuit board 198. Battery 200 provides power to the various elements of sensing unit 164, as described herein. Thus, in an exemplary implementation of the present disclosure, strain gauge 168 communicates force measurements to an input associated with circuit board 198. The circuit board 198 may include processing functionality 203 that is adapted to process the force measurements delivered by strain gauge. The circuit board 198 is also generally associated with transmissive elements, e.g., transceiver elements that include antenna and other components associated with conventional data communications, so as to facilitate transmission and receipt of data associated with measurements and control inputs.

Circuit board 198 may be in communication with one or more components that are adapted to signal users, caregivers and/or healthcare providers as to the condition and operation of the disclosed sensing system. For example, circuit board 198 (and battery 200) may be in electronic communication with a vibration motor 202 that is adapted to be energized in response to control signals received and/or generated by the circuit board 198. For example, if the scoliosis brace associated with sensing unit 161 is insufficiently cinched or otherwise in need of attention/adjustment, circuit board 198 may be programmed to energize vibration motor 202 so as to alert the user of the situation. The vibratory function of vibratory motor may involve a sustained vibratory operation, or pulsed/intermittent vibratory operation, or both depending on the programming of the circuit board.

With further reference to FIG. 4, circuit board 198 may further communicate with one or more LEDs 204 that may be powered to provide data communication to users, caregivers and/or other healthcare providers. In instances where one or more LEDs 204 are included, housing 166 generally includes one or more openings or windows to allow observation thereof. Circuit board 198 may also communicate with a speaker 206 that, when powered, is adapted to provide an aural signal as to performance of the brace system to users, caregivers and/or other healthcare providers. In instances where a speaker 206 is included, housing 166 generally include an opening to allow unobstructed passage of sound therethrough. Thus, the disclosed systems and methods of the present disclosure may be adapted to provide one or more forms of communication as to users, caregivers and/or other healthcare providers, e.g., visually observable communication (e.g., LEDs 204), aural communication (e.g., speaker 206), and/or tactile communication (e.g., vibratory motor 202).

A switch or button 173 is associated with housing 166 to allow users to power up/power down the disclosed sensing system. The switch/button 173 communicates with an associated electronic component 208 that is in electronic communication with circuit board 198 and translates the user interaction to the electronics of the system. The circuit board 198 may also include a USB port 210 that permits porting of data/programming to and from the electronics system. USB port 210 is accessible through an opening 212 defined in housing 166.

As noted above, the disclosed strap and sensing assembly may support a plurality of indicating lights, e.g., LED's, that are adapted to provide a visual signal to users and other caregivers as to the status of a scoliosis brace. The LED's may be aligned in corresponding rows, e.g., along the edges of the housing, and may be adapted to illuminate in different colors based on the orientation/alignment of the associated scoliosis brace. Thus, when the scoliosis brace is properly tightened around the torso of a user, sensing mechanisms associated with the disclosed strap and sensing assembly are adapted to recognize the proper orientation/alignment and to signal that information to the user, e.g., by illuminating one or more "green" LED's. Conversely, if the sensing mechanisms associated with the disclosed strap and sensing assembly determine that the scoliosis brace is not properly oriented/aligned, a warning signal may be provided to the user and other caregivers, e.g., by illuminated one or more "red" LED's. In exemplary implementations, the disclosed assembly may be provided with green, yellow and red LED's to facilitate an indication of brace compliance (with green LED illumination corresponding to strong compliance, red LED illumination corresponding to poor compliance, and yellow LED illumination corresponding to an intermediate level of compliance).

Beyond visual indicators, it is further contemplated that additional and/or alternative communication modalities may be implemented according to the present disclosure. For example, the disclosed strap and sensing assembly may further (or alternatively) include haptic (e.g., vibratory) and/or auditory functionalities for communicating information concerning scoliosis brace usage. The strap and sensing assembly may thus be adapted to deliver vibratory impulses to the user when the brace is improperly positioned, such vibratory impulses varying in intensity and/or frequency as the positioning/alignment of the brace is adjusted. Similarly, the disclosed strap and sensing assembly may be adapted to deliver vibratory impulses to the user when the brace is properly positioned, such vibratory impulses varying in intensity and/or frequency as the positioning/alignment of the brace is adjusted. The disclosed strap and sensing assembly may also include an aural transmitter that is adapted to transmit sound-based signals to the user based on brace positioning and/or usage, with differing aural signals based on relative positioning of the brace. The breadth and flexibility of the communication modalities that may be implemented according to the present disclosure will be readily apparent to persons skilled in the art in view of the present disclosure.

Of note, the disclosed strap and sensing assemblies that are adapted to provide advantageous monitoring and feedback functionality according to the present disclosure may be incorporated into newly constructed and prescribed scoliosis brace systems, or retrofitted onto existing scoliosis brace systems. Indeed, although individual scoliosis braces are custom fabricated for specific users, the strap-based elements of scoliosis brace systems are relatively uniform and therefore well adapted for retroactive transition to the monitoring/feedback system of the present disclosure. Thus, the disclosed monitoring/feedback functionalities may be widely adapted at minimal expense to users and/or health care providers.

With reference to FIG. 5, a side view (partially in section) of an exemplary implementation of the disclosed strap and sensing assembly in conjunction with a scoliosis brace. For illustration purposes, the exemplary implementation of FIG. 5 is based on the embodiment of FIG. 2. As shown therein, strap 162 is mounted with respect to portion 104 of a scoliosis brace (by screw 109') and strap 108 is mounted with respect to portion 102 (by screw 109). Sensing assembly 114 is mounted with respect to strap 162, at least in part by mounting arm/screw 191. Portions 102, 104 of the disclosed scoliosis brace are cinched relative to each other by routing of strap 108 around rod/pin 177. Once the cinching is complete, strap 108 is fixed, e.g., based on Velcro® securement relative to itself. A magnet 220 is mounted with respect to strap 108 and provides advantageous functionality as discussed in greater detail below.

Turning to FIG. 6 and FIGS. 7A and 7B, top views of exemplary implementations of the disclosed strap and sensing assembly in conjunction with scoliosis braces are provided. FIG. 6 depicts a strap assembly 200 includes a "resistance-based" sensing system. FIGS. 7A and 7B depict a strap assembly 250 that includes a "magnetic-based" sensing system in two cinching positions. Each of the disclosed sensing systems is adapted to monitor/measure the position of the strap, e.g., when used to cinch a scoliosis brace around the torso of a user. The sensing parameter may be compared to a target reading to determine whether the scoliosis brace is properly tightened (subject to applicable tolerances). Based on such comparison, a signal may be delivered to the user and associated caregivers (e.g., a visual, haptic and/or aural signal). Moreover, the determination may be stored in a database for use in various analytic and/or diagnostic functions, e.g., assessing the degree to which a scoliosis brace has been properly employed by a user.

With further reference to FIG. 6, exemplary strap assembly 200 includes a sensing unit 202 that is mounted with respect to a strap 204 and that cooperates with a second strap 206 to facilitate cinching of a brace (not pictured). First and second conductive strips 208, 210 are embedded or otherwise associated with strap 206 which is fabricated (at least in part) from a resistive fabric. The fabric-based circuit acts as a custom, flexible linear potentiometer. An electronics module is incorporated into or otherwise associated with sensing unit 202. The electronics module is adapted to amplify the signal generated based on a resistance change between opposed points along conductive strips 208, 210. The rod/pin 212 around which strap 206 passes is also conductive and bridges conductive strips 208, 210 when the strap assembly 200 is used to secure a scoliosis brace relative to a user. As the conductive rod/pin 212 bridges the two conductive strips 208, 210, the resistance changes linearly. Indeed, the system functions as a Wheatstone bridge, generating a signal based on the relative positioning of the elements. Thus, the resistance measured by the disclosed system will vary based on the position of strap member 206 relative to conductive rod/pin 212, i.e., the degree to which strap member 206 is "cinched" in securing the scoliosis brace relative to a user's torso. Of note, the signal generated by the disclosed resistance measurement may be amplified (e.g., using a Texas Instruments INA126 amplifier) and transmitted to an analog-to-digital converter associated with a microcontroller, as described in greater detail below.

Turning to FIGS. 7A and 7B, exemplary strap assembly 250 that includes a sensing unit 252 that is mounted with respect to a strap 254 and that cooperates with a second strap 256 to facilitate cinching of a brace (not pictured). Magnetic sensors are embedded or otherwise associated with sensing unit 252 (not pictured) and are configured/positioned so that as the output voltage of one magnetic sensor associated with sensing unit 252 increases and the output voltage of the second magnetic sensor associated with the sensing unit 252 decreases as the magnet 270—which is embedded or otherwise associated with a region toward or at the other end of the strap 256—moves relative to sensing unit 252. Thus, the difference between the two output voltages generated by the magnet sensors associated with sensing unit 252 increases as magnet 270 moves closer to the sensing unit 252, i.e., the difference in output voltage measured by the disclosed system will vary based on the position of strap member 256 relative to sensing unit 252, i.e., the degree to which strap member 256 is "cinched" in securing the scoliosis brace relative to a user's torso. As with the resistance-based implementation described above, the signal generated by the disclosed output voltage measurement may be amplified and transmitted to an analog-to-digital converter associated with a microcontroller, as described in greater detail below.

As disclosed herein, the strap-based system may include strain gauge functionality that functions to measure the force level experienced by the strap. Thus, two strain gauges may be provided. A beam may be associated with the strain gauges such that beam bending correlates with a linear force applied to or experienced by the strap. The strain gauges may be positioned in the region of bending such that a Wheatstone bridge is established therebetween. The strain-based signal generated by the Wheatstone bridge may be compared to reference data to determine whether the strap force is within a prescribed range. Moreover, changes in the signal may be monitored to assess performance of a scoliosis brace over time. The strain-based signal generated by the Wheatstone bridge may be fed to a differential instrumentation amplifier which may be adapted to amplify the signal, e.g., to a level that may be read by an analog-to-digital converter associated with a microcontroller, as described in greater detail below. As with the "cinching" measurements described above, the strain-based measurements may be stored in a database for use in various analytic and/or diagnostic functions, e.g., assessing the degree to which a scoliosis brace has been properly employed by a user. Alternative systems may be used to monitor and/or measure forces experienced by the disclosed strap, as will be readily apparent to persons skilled in the art.

Figure 8:
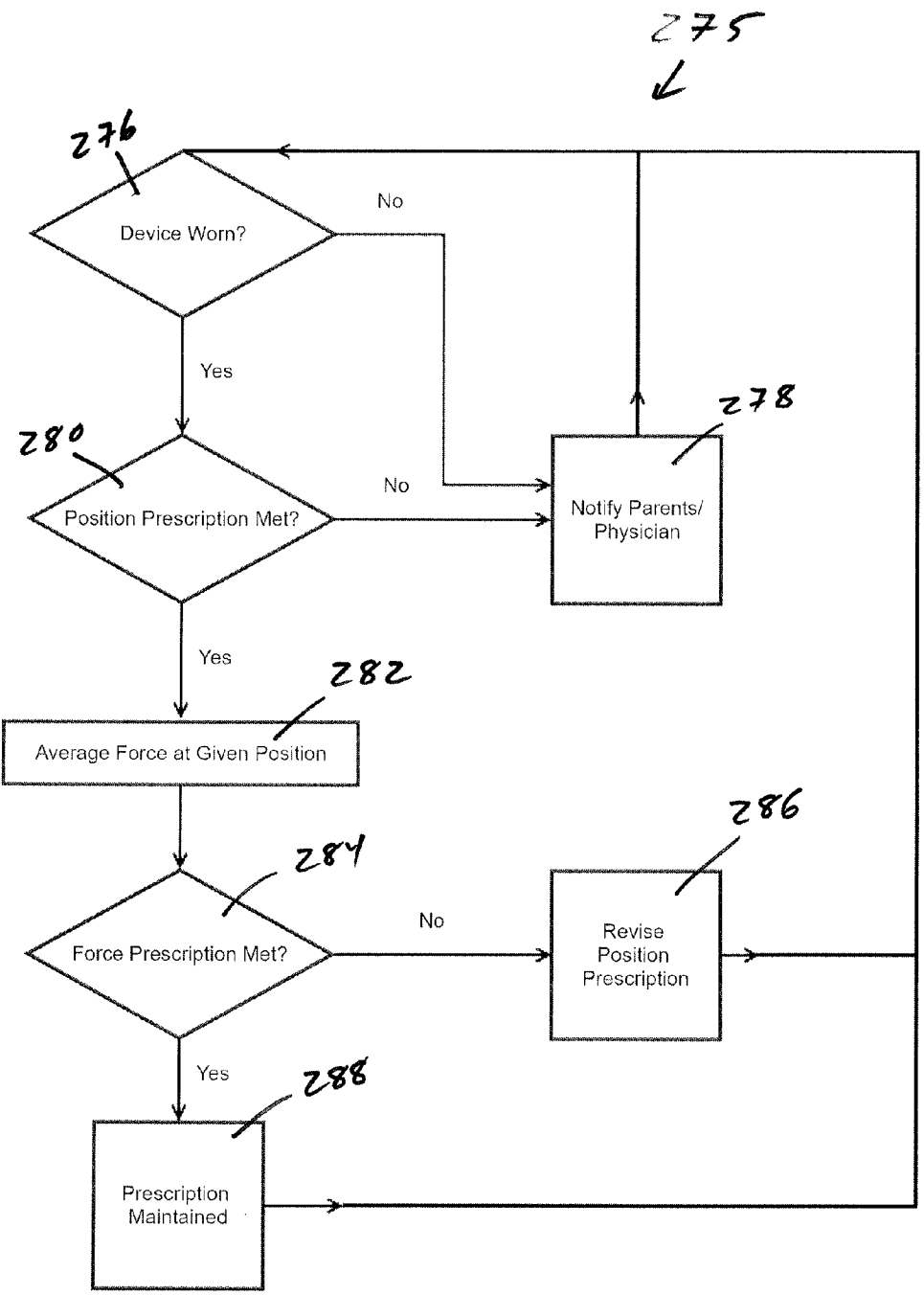
FIG. 8 is a flowchart of showing exemplary determination parameters associated with the brace-based sensing system of the present disclosure.

FIG. 8 provides an exemplary flowchart 275 that illustrates a sequence of steps by which the disclosed system/method may be determine quality and compliance of brace use. Thus, as shown in FIG. 8, the system/method may determine whether the brace is being worn (Step 276). If not, the parents and/or physician may be notified (Step 278). Conversely, if the device is being worn, the system/method determines whether the prescription as to brace positioning is being satisfied (Step 280). If not, the parents and/or physician may be notified (Step 278). If so, the average force at the applicable brace position is determined (Step 282). Based on the average force determination, the system/method determines if the prescription as to force is being met (Step 284). If not, the position prescription is revised to deliver the desired force level (Step 286). Conversely, if the force prescription is being met, then the prescription level is maintained (Step 288) and the system/method rechecks quality/compliance, as and when prompted, e.g., based on a preset frequency schedule.

Figure 9:
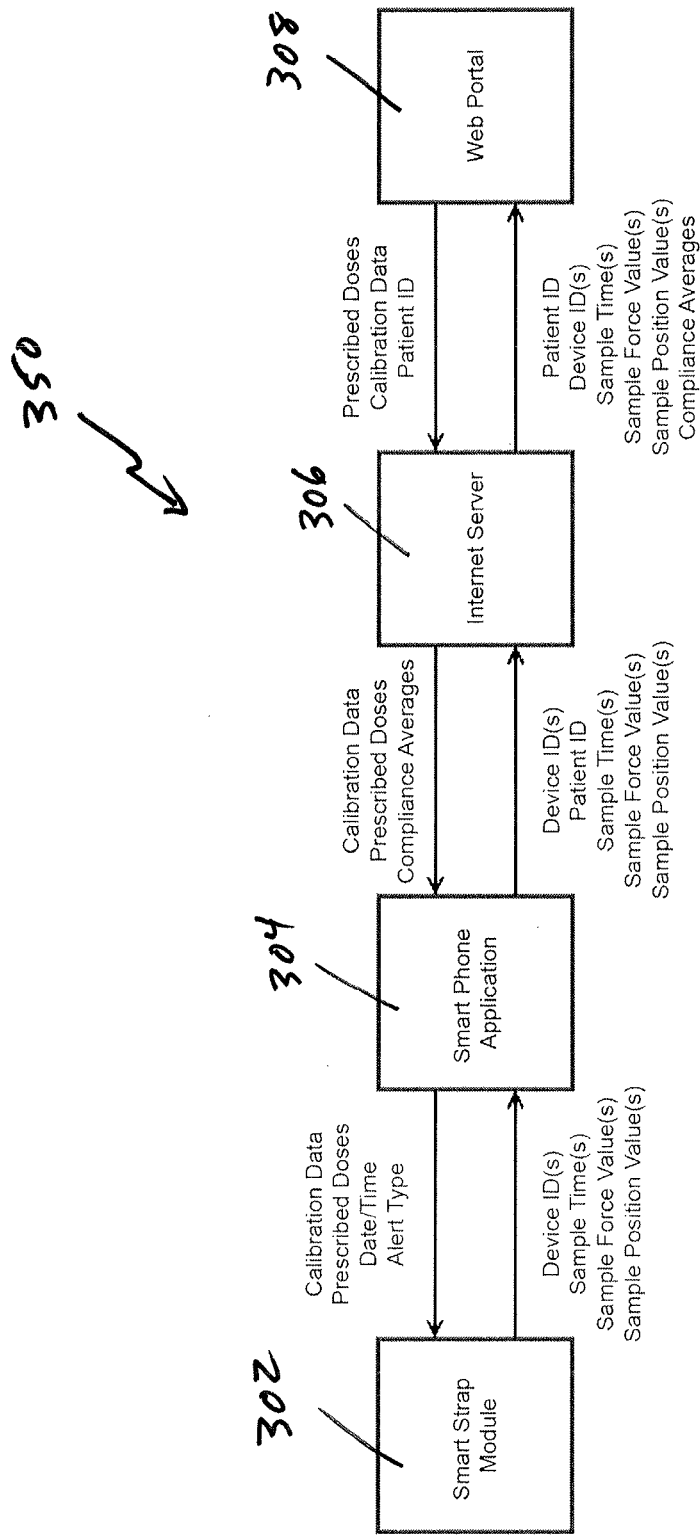
FIG. 9 is a flowchart of exemplary data exchange modalities according to the present disclosure.

FIG. 9 provides a schematic flowchart 350 of exemplary data flow according to implementations of the present disclosure. As shown in FIG. 9, the flow of data according to the present disclosure generally begins in the strap-based device/system ("Smart Strap Module 302"), where the force and/or position sensors are located. The device generally measures and/or captures sample time(s), sample force value(s) and sample position value(s). Data may be shuttled to a Bluetooth module for transmission to external devices, e.g., a computer or smartphone interface ("Smart Phone Application 304"). The Smart Phone Application 304 can in turn communicate with an Internet Server 306 that then communicates with a Web Portal 308. Communications may proceed in the opposite direction, i.e., originating from the Web Portal 308 and ultimately reaching the Smart Strap Module 302, e.g., prescribed does, calibration data, and patient ID. Thus, the Web Portal may be associated with an external device to facilitate transfer of the data to a web-based database and associated processing capabilities. In addition, the Web Portal 308 may support access and use of the data by interested parties, e.g., physicians, patients, parents and operational centers ("109Design").

Thus, the disclosed device components may include sensors that are adapted to monitor and/or measure position (e.g., the resistance and magnetic systems described above) and/or tension/force (e.g., the strain gauge systems described above). The parameters measured by the disclosed sensors may be processed by a microcontroller associated with a circuit board that generally includes programming to drive the features and functions described herein. The device components also generally include appropriate data storage, e.g., a memory card such as a Micro-SD (secure digital) non-volatile memory card.

Once the microcomputer receives information from the sensor(s), the microcomputer may be programmed to actuate a variety of immediate feedback mechanisms, e.g., to notify the patient/user when certain conditions are met. Feedback mechanisms may be selected by the patient/user and customized depending on applicable variables, e.g., the type of scoliosis brace, the needs of the patient/user, the age/maturity of the patient/user and the like.

The device components also generally include one or more features/functions that are adapted to provide immediate feedback to users/caregivers with respect to scoliosis brace use and performance. Thus, as described above, the disclosed system may include device components that are adapted to generate and deliver light signals, haptic/vibratory signals and/or sound-based signals. For example, RGB LED lights may be adapted to deliver feedback to the patient/user by changing color, intensity and/or the number of lights that are illuminated. In exemplary embodiments, the color of illumination light and/or aspects of the illumination (e.g., blinking rate) may be used to communicate information concerning the quality of scoliosis brace usage, as described with reference to previous embodiments. For example, a green LED may be illuminated if the quality of usage is good, a red LED may be illuminated if the quality of use is poor, and a yellow LED may be illuminated if the quality is of intermediate quality. Similarly, rapidity at which the LED is blinked may be used to signal proximity to a desired (or undesired) position of the scoliosis brace. Auditory feedback may be delivered in various ways, e.g., a piezoelectric buzzer may be used to alert a patient/user of a sensed condition even if the patient/user is not looking at the brace. Haptic/vibratory feedback may be particularly valuable to patients/users because the straps of a scoliosis brace are often located adjacent the patient's back, which means that the patient will not be able to see visual feedback associated with the strap(s). Haptic/vibratory feedback may also be generated and delivered in a manner that is not apparent to others in the vicinity, thereby preserving the privacy of the patient/user.

Still further, device components associated with the present disclosure generally include elements that are adapted to support data transmission, e.g., a Bluetooth module. For example, the microcontroller of the disclosed system may be adapted to relay stored data to the Bluetooth module for output in a serial stream that can be received and read by smartphones, computers and other Bluetooth-enabled electronic devices/systems. Power is generally delivered to the disclosed device components by appropriate battery technology, e.g., rechargeable lithium polymer battery. Charging of the disclosed battery may be accomplished by way of a micro-USB connection and/or internal charging circuitry associated with the disclosed system. Information generated by the disclosed device components are advantageously transmitted, e.g., by way of a Bluetooth communications, to external processing and/or data storage units. Bluetooth transmissions may be employed to transmit information that is sensed and processed by the device components to external systems, such as an external computer and/or smartphone.

In addition, the information that is transmitted from the disclosed device components may be routed to a network-based system, such as an online database and associated processing functionality. In exemplary implementations, the information that is collected by the device components associated with a scoliosis brace system may be routed to an application that permits access by a physician and/or other health care provider, thereby permitting scoliosis-related assessments and adjustments to be undertaken in a timely and effective manner without the need for frequent office visits by the patient. Interaction with and analysis of the data generated by the disclosed systems may be facilitated by appropriate user interfaces that are programmed to deliver user-friendly information display and associated processing tools. Different user interfaces may be provided for different user groups, e.g., patients and physicians/health care providers.

The information that is transmitted to external systems and the immediate feedback generated by the device components, e.g., visual, haptic and/or sound communications, may benefit the patients, their parents (and other caregivers) and doctors (and other health care providers). Still further, research organizations and/or central monitoring organizations (e.g., "109Design") may have access to or otherwise receive information that is generated according to the present system.

Figure 12:
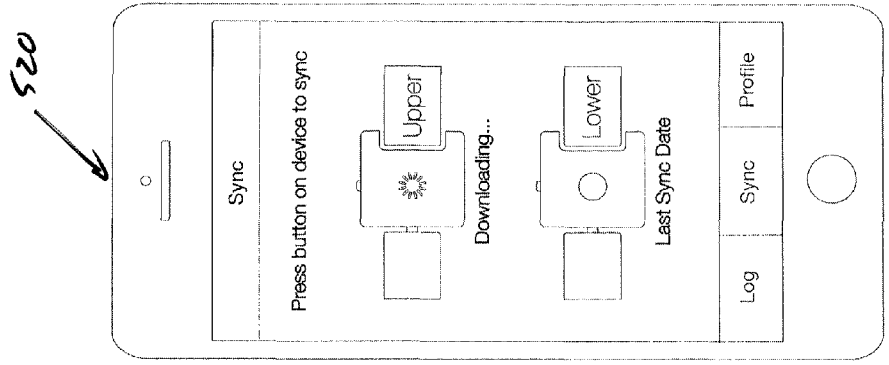
FIG. 12 is an exemplary depiction of a synchronization display according to the present disclosure.
Figure 11:
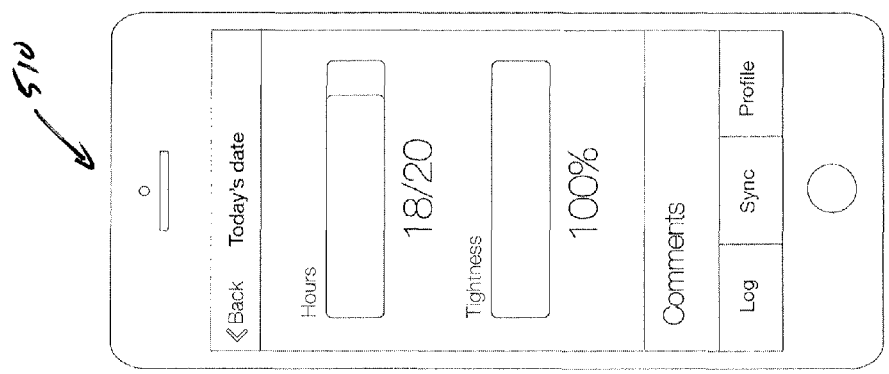
FIG. 11 is an exemplary depiction of a further data display associated with daily use of the brace-based system of the present disclosure.
Figure 10:
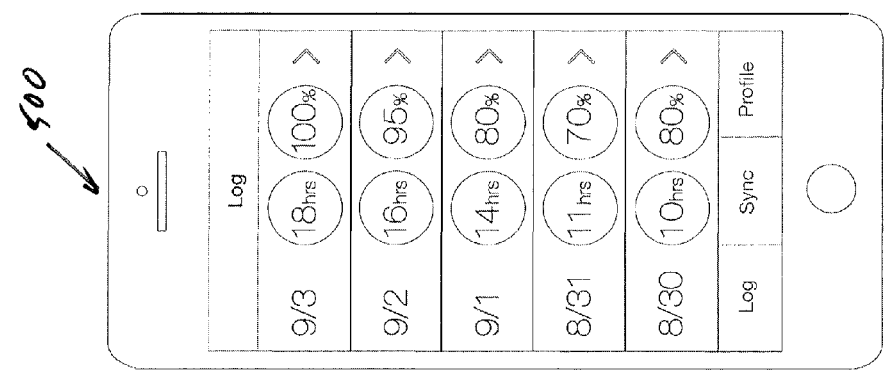
FIG. 10 is an exemplary depiction of a data display associated with a period of use of the brace-based system of the present disclosure.

With reference to FIGS. 10-12, exemplary data displays that are supported by the monitoring/measuring and feedback systems of the present disclosure are illustrated, as follows:

FIG. 10 depicts an exemplary screenshot 500 that may be displayed through an user interface according to the present disclosure. As shown along at top of the screenshot, a "log" link is provided that allows review of the user's usage log. Below the "log" link, the display shows exemplary brace usage for a series of days (8/30-9/3), including specifically the number of hours of brace usage and the tightness relative to prescribed level (as a percentage). Thus, on 9/3, the exemplary screenshot shows that the user wore the brace for "18 hrs" at an average tightness relative to prescription of "100%". This usage relative to prescriptive usage was dramatically better than the performance, for example, on 8/31 when the brace was only worn for 11 hours and the tightness level (on average) during that period of usage was only "70%" of the prescriptive tightness level. Further links are provided at the bottom of display 500, namely "log", "sync" and "profile" links. The "log" link provides access to the user's usage log, the "sync" link prompts synchronization with ancillary systems, e.g., an associated phone and/or web profile, and the "profile" link provides access to a profile page for the user.

FIG. 11 depicts a further exemplary screenshot 502 that shows usage data for "today's date," i.e., hours of brace usage and "tightness" data relative to prescription. In the exemplary screenshot 502, more detailed log information relative to brace usage on 9/3 on FIG. 10 is provided. Thus, as shown on screenshot 502 on FIG. 11, the 18 hours of brace usage was relative to 20 hours of prescribed usage (i.e., "18/20"). The screenshot 502 of FIG. 11 also includes a series of links which correspond to the links associated with screenshot 500 depicted in FIG. 10.

FIG. 12 depicts a further exemplary screenshot 504 that provides synchronization functionality. As set forth on screenshot 504, synchronization is supported with respect to each of the strap assemblies. Thus, screenshot 504 relates to a two strap system and, as shown, the upper strap system is in the process of downloading, whereas the lower strap system, the "last sync date" is displayed.

Figure 13:
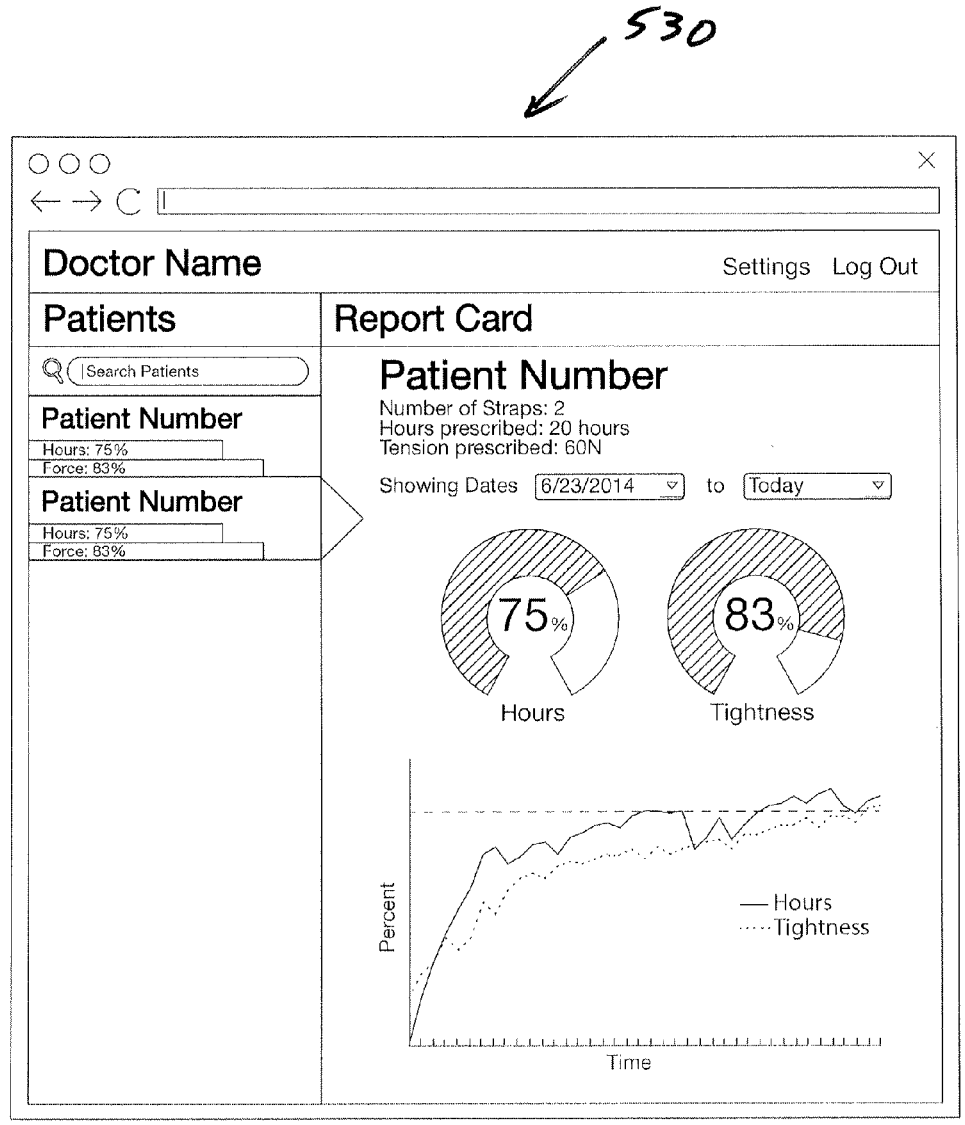
FIG. 13 is an exemplary depiction of a patient record display according to the present disclosure.

FIG. 13 provides a further exemplary screenshot 530 that captures overall compliance/quality usage information for a given doctor pursuant to the present disclosure. Thus, for example, screenshot 530 displays the prescribing "doctor name" and summary information along the left-side column—a search box for use in locating a particular patient of interest and summary information for a given patient (hours—75%; force—83%). To the right of the left-side column, more detailed information relative to the particular patient, i.e., number of straps—2; hours prescribed—20 hours; tension prescribed—60 N. The graphic display toward the bottom of screenshot 530 illustrates usage data over time, both as to "hours" (solid line) and "tightness" (dashed line). According to exemplary embodiments of the present disclosure, force measurements are averaged and compared to brace positioning, i.e., spacing or overlap. Of note, "force" is the clinical parameter of relevance for prescriptive purposes (e.g., 60 N), but spacing of the brace is the parameter generally a more effective control parameter for instantaneous feedback.

The screenshot 530 is particularly advantageous for a doctor to quickly and efficiently assess brace usage for his/her patients. Based on this patient-specific information, the physician is able to determine whether action is required relative to the patient, e.g., revisions to prescriptive "time" and/or "tightness". Moreover, the physician would be able to determine whether a follow-up visit with the patient is required. It is further contemplated that the systems/methods of the present disclosure may support and/or facilitate an incentive and/or reward program based on patient usage. For example, the disclosed system/method may permit establishing usage threshold(s), e.g., 90% usage at desired force level, and generating an associated reward, e.g., gift certificate or the like.

The present disclosure has been described with reference to various exemplary implementations and embodiments of the advantageous systems and methods for monitoring and/ or measuring parameters related to the use of braces, e.g., compliance and quality of scoliosis brace usage. However, the present disclosure is not limited by or to the exemplary implementations and embodiments described herein. Rather, the systems and methods of the present disclosure are susceptible to many alternative implementations and embodiments without departing from the spirit or scope provided herein, as will be readily apparent to persons skilled in the art. Accordingly, the present disclosure expressly encompasses and embraces such alternative implementations and embodiments within its scope.

The invention claimed is:

1. A method for acquiring information concerning quality and compliance of scoliosis brace usage, comprising:
   a. providing a scoliosis brace defining a first brace portion, a second brace portion, and an interface region between the first brace portion and the second brace portion, wherein the scoliosis brace includes:
      i. a first strap mounted with respect to the scoliosis brace;
      ii. a first sensing assembly mounted with respect to the scoliosis brace on an opposite side of the interface region relative to the first strap, wherein the first sensing assembly is physically engaged with the first strap;
      iii. a second strap mounted with respect to the scoliosis brace; and
      iv. a second sensing assembly mounted with respect to the scoliosis brace on an opposite side of the interface region relative to the second strap, wherein the second sensing assembly is physically engaged with the second strap;
   b. manually tightening the first strap relative to the first sensing assembly to adjust relative positioning of the first brace portion and the second brace portion proximate the first sensing assembly;
   c. manually tightening the second strap relative to the second sensing assembly to adjust relative positioning of the first brace portion and the second brace portion proximate the second sensing assembly;
   d. acquiring first force data from the first sensing assembly, wherein the first force data corresponds to tension applied to the first sensing assembly by physical engagement with the manually-adjusted first strap;
   e. acquiring second force data from the second sensing assembly, wherein the second force data corresponds to tension applied to the second sensing assembly by physical engagement with the manually-adjusted second strap;
   f. using a processor in communication with the first sensing assembly and the second sensing assembly, comparing (i) the first force data to a predetermined force parameter to determine quality of brace usage proximate to the first sensing assembly, and (ii) comparing the second force data to the predetermined force parameter to determine quality of brace usage proximate to the second sensing assembly;
   g. acquiring compliance data from at least one of the first sensing assembly and the second sensing assembly that corresponds to temporal usage of the brace; and
   h. displaying the first force data, the second force data and the compliance data for review.

2. The method according to claim 1, further comprising signaling a user or health care provider relative to compliance or quality of brace usage based on at least one of the first force data, the second force data and the compliance data.

3. The method according to claim 1, wherein the first sensing assembly and the second sensing assembly include at least one of a strain gauge mechanism and a magnet and sensor mechanism.

4. The method according to claim 1, further comprising mounting the first sensing assembly and the second sensing assembly to a scoliosis brace.

5. The method of claim 1, wherein the first sensing assembly includes a first device loop that is sized to receive a free end of the first strap therethrough, and wherein the second sensing assembly includes a second device loop that is sized to receive a free end of the second strap therethrough.

6. The method of claim 5, wherein a strain gauge is associated with the first device loop to measure force exerted by the first strap relative to the first device loop.

7. The method of claim 1, wherein the first strap includes one or more magnets mounted with respect thereto, wherein the first sensing assembly includes one or more sensors mounted with respect thereto, and wherein relative positioning of the magnets and the sensors is used by the processor to generate first force data.

8. The method of claim 1, further comprising electronic elements associated with and in communication with the first sensing assembly for processing information generated by the first sensing assembly.

9. The method of claim 8, wherein the electronic elements include a power source and the processor.

10. The method of claim 8, further comprising means for communicating the information generated by the first sensing assembly to an external device.

11. The method of claim 1, further comprising means for performing analytics relative to the first force data, the second force data and the compliance data.

12. The method of claim 1, further comprising one or more signaling elements for delivering information to a user or health care provider relative to compliance and quality of scoliosis brace usage.

13. The method of claim 12, wherein the one or more signaling elements is adapted to provide real-time feedback as to tightness of positioning of the at least one of the first strap and the second strap.

14. The method of claim 12, wherein the one or more signaling elements comprises aural, visual and haptic signaling elements associated with at least one of the first sensing assembly and the second sensing assembly.

15. The method of claim 12, wherein the signaling elements comprise one or more LEDs that are adapted to deliver light signals of differing colors based on compliance and quality of scoliosis brace usage.

* * * * *